United States Patent
Gupta et al.

(10) Patent No.: US 6,869,625 B2
(45) Date of Patent: Mar. 22, 2005

(54) METHOD OF TREATING DIABETES USING PLANT ARGYROLOBIUM ROSEUM EXTRACT, AND A PROCESS FOR THE ISOLATION OF EXTRACT FROM THE SAID PLANT

(75) Inventors: Om Prakash Gupta, Jammu (IN); Zabeer Ahmed, Jammu (IN); Asha Bhagat, Jammu (IN); Kuldeep Kumar Gupta, Jammu (IN); Sukhdev Swami Handa, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 128 days.

(21) Appl. No.: 10/267,040

(22) Filed: Oct. 9, 2002

(65) Prior Publication Data

US 2003/0086985 A1 May 8, 2003

Related U.S. Application Data

(60) Provisional application No. 60/327,285, filed on Oct. 9, 2001.

(51) Int. Cl.[7] .......................... A61K 35/78; A01N 25/00
(52) U.S. Cl. ....................................... 424/757; 514/866
(58) Field of Search .................. 424/757; 514/866; 425/725; 536/8

(56) References Cited

U.S. PATENT DOCUMENTS 5,532,256 A * 7/1996 Malamas et al. ........... 514/361
5,804,206 A * 9/1998 D'Amelio et al. .......... 424/401

OTHER PUBLICATIONS

Chaudhary, L B, Journal or Economnc & Taxonomic Botany (1997), 21(1): 211–222. Revision of Argyrolobium Eckl. & Zehy. (Papilionoideae) of India.*
Hooker, Flora of British India, vol. 11, p. 63.
H.J. Chowdhury & B.M. Wadhwa, Flora of Himachal Pradesh, p. 181–182.
Chapman and Hall, Dictionary of Natural Products, vol. 7, p. 414, 1994.
Chapman and Hall, Dictionary of Natural Products, vol. 1, p. 457, 1994.
Index Kewerisis, vol. 1, p. 184, 1895.
Orn Prak ash Vidyarthl, Wild & Cultivated Plants of Jammu & Kashmir and Ladakh, p. 23, 1997.
F. Nasir, Flora of West Pakistan, p. 385, vol. 100.
Flora of Jammu & Plants of Neighborhood, vol. 11, Plate 64, p. 181–182, 1983.
Nair. Flora of Bashahr Himalaya, p. 69, 1997.

* cited by examiner

*Primary Examiner*—Michele Flood
(74) *Attorney, Agent, or Firm*—Foley & Lardner LLP

(57) ABSTRACT

The present invention relates to a process for isolating plant *Argyrobium roseum* extract that contains flavonoid glycoside, wherein the extract possesses hypoglycaemic activity. The present invention also contemplates a composition containing the extract and a method of treating various hyperglycaemic conditions including non-insulin dependent diabetes mellitus disease condition by administering the extract.

19 Claims, No Drawings

METHOD OF TREATING DIABETES USING PLANT ARGYROLOBIUM ROSEUM EXTRACT, AND A PROCESS FOR THE ISOLATION OF EXTRACT FROM THE SAID PLANT

This application claims priority to U.S. provisional application Ser. No. 60/327,285, filed on Oct. 9, 2001; the entirety of which is incorporated herein by reference.

FIELD OF THE INVENTION

The present invention relates to an antidiabetic extract obtained from the plant, *Argyrolobium roseum*, methods for isolating the extract, and use of the extract for treating patients that have hyperglycemic-related diseases or conditions.

BACKGROUND

*Argyrolobium roseum* is a herb or shrub found in the tropical and sub-temperate tracts of north-western India. The plant grows, for instance, in the hilly area of Udhampur district of Jammu and Kashmir, India, where it typically flowers and bears fruit between April and June. (see Chowdhary and Wadhwa, FLORA OF HIMACHAL PRADESH pp 181–1821; Chapman and Hail, DICTIONARY OF NATURAL PRODUCTS, Vol. 7, 414, 1994. Vol. 1, 457, 1994; Index Kewensis, Vol. 1, 184, 1895; Om, WILD AND CULTIVATED PLANTS OF J&K AND LADAKH, Page 23, 1997).

Descriptions of *Argyrolobium* plants can be found in FLORA OF WEST PAKISTAN, Page 385, volume 100, by E. Nasirl; FLORA OF THE HIMALAYA, Page 94, Plate No. 323, d 460, by Oleg Polunin, Adam Staintonj; FLORA OF JAMMU AND PLANTS OF NEIGHBOURHOOD Volume II, 1983, Plate 64, Page-180–1821; FLORA OF LHMACHAL PRADESH, Page 181–182, By H. J. Chowdhary and B. M. Wadhwal; FLORA OF BASHAHR ITMALAYAS, Page 69, 1997, by N. C. Nairl; and FLORA OF BRITISH INDIA, Vol. II, Page 63, by Hooker. Other species of *Argyrolobium* include *Argyrolobium megharizum* and *Argyrolobium flaccidum* (DICTIONARY OF NATURAL PRODUCTS, Vol. 1, 457, 1994, By Chapman & Hall). However, there have been no reports that *Argyrolobium roseum* has any medicinal or biological uses for animals or mammals such as humans. Specifically, there has been no description of the use of this natural product to treat hyperglycemic conditions.

SUMMARY

The present invention relates to a process for isolating an *Argyrobium roseum* extract that possesses hypoglycemic activity and which contains a flavonoid glycoside compound. The present invention also encompasses a composition comprising the extract suitable for administration to an animal, and also a method of treating various hyperglycemic conditions such as non-insulin dependent diabetes mellitus (NIDDM), by administering that composition.

One object of the present invention, then, is a method for isolating an extract from a *Argyrolobium roseum* plant, wherein the extract has hypoglycemic activity and contains a flavonoid glycoside compound. That extract can be formulated, such as into tablet form, into a composition useful for treating hyperglycemia and NIDDM in animals, including humans. Further, the present invention contemplates the admixing of other hypoglycemic agents and additives in a formulation comprising the inventive extract composition.

An object of the present invention, then, is to develop a method of treating hyperglycemia and NIDDM in animals, such as mammals, by administering an extract isolated from *Argyrolobium roseum*, wherein the extract contains a flavonoid glycoside compound. A human, for example, can be treated with the extract, so long as the extract or formulated composition does not induce any harmful side effects in the animal, mammal or human. Other hypoglycemic agents and additives may be co-administered with the inventive *A. roseum* extracted composition. Another object of the present invention is to develop a dosage regime for treating hyperglycemic disease conditions like diabetes.

DETAILED DESCRIPTION

Accordingly, the present invention relates to a method of treating hyperglycemia and NIDDM in animals including humans, by administering an effective amount of extract from plant *Argyrolobiwn roseum* containing compound flavonoid glycoside, or by administering the compound flavonoid glycoside per se. The present invention shows that model animals treated with the inventive extract composition overcame hyperglycemic disease-associated symptoms. Indeed, the present invention uses, for the first time, an *Argyrolobium roseum* extract to treat hyperglycemic diseases such as diabetes mellitus, which afflicts all levels of society world-wide. In doing so, the present invention provides a natural, plant-based, non-toxic herbal preparation that can be used to treat diabetes mellitus. The extract can be easily prepared by isolating the particular plant powder using solvents and then vacuum-dried, without losing antidiabetic activity. Furthermore, there was no undesirable side effects in animals that had been treated with up to 2000 mg/kg p.o. doses of the extract. Accordingly, the antidiabetic activity of the extract can be used to control hyperglycemia and particularly NIDDM.

Pharmaceutically acceptable additives can also be co-administered with the extract. Suitable additives include, but are not limited to a group of nutrients comprising proteins, carbohydrates, sugar, talc, magnesium sterate, cellulose, calcium carbonate, starch-gelatin paste, and/or pharmaceutically acceptable carrier, excipient, diluent, solvent and other hypoglycemic agents.

In another embodiment of the present invention, wherein the effective amount of the inventive extract may be a dosage that ranges from about 1 to about 3000-mg/kg p.o./day; wherein the dosage regime may be continued for about 2 to about 4 weeks. Preferably, the effective amount is a dose that ranges between about 200 to about 1000 mg/kg p.o./day over about 2–4 weeks of treatment.

The beneficial effects of the administered extract should last for about 8 hours once administered to the animal or mammal. Indeed, the inventive extract composition can be about 20 times more effective as compared to the whole extract, without inducing undesirable side effects in that animal or mammal.

Thus, the present invention provides a composition useful for treating hyperglycemia and NIDDM in animals including humans, said composition comprising an effective amount of extract from the plant *Argyrolobium roseum*, containing compound flavonoid glycoside or compound flavonoid glycoside per se, optionally along with additives.

In another embodiment of the present invention, the additives are selected from a group of nutrients comprising proteins, carbohydrates, sugar, talc, magnesium sterate, cellulose, calcium carbonate, starch-gelatin paste, and/or pharmaceutically acceptable carrier, excipient, diluent, solvent, and other hypoglycemic agents. Typically, the additives are not detrimental to the beneficial properties of the extract. In yet another embodiment of the present invention, the composition is administered orally as a capsule, tablet, syrup, concentrate, powder, granules, aerosol, or beads.

The present invention also envisions a process for isolating an extract from plant *Argyrolobium roseum*, which extract contains a flavonoid glycoside compound and has hypoglycemic activity. That method may comprise:

(a) drying the whole plant in powder form,
(b) percolating the powder about 3–5 times with polar or non-polar solvents,
(c) macerating the extract,
(d) obtaining the macerated extract of yield ranging between 7–10%,
(e) drying the extract in vacuum,
(f) isolating the pure compound flavonoid glycoside by chromatography, and,
(g) obtaining the compound flavonoid glycoside in the range of 0.015–0019%.

In another embodiment of the present invention, wherein the said compound is isolated by column chromatography on silica gel 60–120 microns mesh size.

In still another embodiment of the present invention, wherein macerating the extract with compound selected from a group comprising hexane, ethyl acetate, acetone, chloroform.

In still another embodiment of the present invention, wherein preferred solvents for percolation are alcohols and acetones.

In still another embodiment of the present invention, the flavonoid glycoside itself is purified from the extract and used for preparing a pharmaceutical composition for treating non-insulin dependent diabetes in mammals and human beings.

In still another embodiment of the present invention, wherein said compound flavonoid glycoside having significant hypoglycaemic activity.

In still another embodiment of the present invention, the compound alcoholic extract having the activity of regeneration of β-cells of pancreas in streptozotocin treated rats.

In still another embodiment of the present invention, the flavonoid glycoside isolated from *Argyrolobium roseum* can be used at 20 times less dose, i.e. 10 mg as compared to 200 mg/kg p. o. dose of alcoholic or acetone fraction of the plant showed significant hypoglycaemic activity.

In still another embodiment of the present invention, wherein the aqueous extract, alkaloidal and non-alkaloidal fractions do not possess any significant hypoglycaemic activity.

The invention is described in the examples given below which are provided by a way of illustrations only and should not be construed to limit the scope of the present invention.

EXAMPLES

Example-1

The dose of streptozotocin is used to induce diabetes mimicking to NIDDM, encountered clinically in Majority of patients. The NIDDM diabetic rats when treated with alcoholic extract of the plant *Argyrolobium roseum*, for 2–3 weeks recovered to normal state, whereas the rats of control NIDDM diabetic group continued to have diabetes and died in due course of time.

Example-2

1 kg of *A. roseum* (whole plant) is shade dried and powdered. The powdered plant material was extracted with ethyl alcohol (5 litres) for 20 hours. The alcohol extract was vacuum dried. The yield was 91 gms. The dried alcoholic extract was macerated successively with hexane and chloroform to give 8.2 gms. and 39.3 gms. of the extracts respectively. A flavonoid glycoside (230 mgs) was isolated from the chloroform extract by repeated column chromatography over silica gel of mesh size 60–120 micron. The extract (200 mg/kg p.o.) showed significant hypoglycaemic activity as tested on normal, 18 h fasting, glucose loaded & streptozotocin induced hyperglycaemic rats. The onset of effect within ½ h and the effect lasted for more than five hours. The fall of blood sugar recorded with above dose was 26 mg/dl (n=24) as compared to fall of 17 & 23 mg/dl recorded with tolbutamide, 50 mg/kg p.o. (n=9) and glipizide, 0.5 mg/kg p.o. (n=8) respectively in 18 h fasting rats.

The hypoglycaemic activity was also recorded with plant powder (2.5 g/kg p.o.) and flavonoid glycoside isolated from the plant.

Example-3

1 kg of *A. roseum* (whole plant) is dried and powdered. The powdered plant material was percolated four times with 95% methyl alcohol (3 lit. each time). The alcohol extract was vacuum dried 85 gms. The alcohol extract was macerated successively with hexane and acetone to give 6.7 gms. and 49.6 gms. of the extracts respectively. A flavonoid glycoside (170 mgs) was isolated from the acetone extract by repeated column chromatography over silica gel of mesh size 60–120 micron. There was highly significant recovery of rats from non-insulin dependent diabetes mellitus treated with the extract (200 mg/kg p.o./day) for 2–3 weeks as per with following parameters: i) Blood glucose level, ii) Effect on body weight, iii) Survival of the animals, iv) Water intake, urine output & presence of glucose in urine, v) General condition of the animals and vi) Visit of ants to the voided urine of the rats.

Example-4

1 kg of *A. roseum* (whole plant) was shade dried and powdered. The powdered plant material was percolated four times with 95% acetone (3 lit each time). The acetone extract was vacuum dried. The yield was 87 gms. The alcoholic extract was macerated successively with hexane and ethyl acetate to give 7.2 gms and 42.8 gms of the extracts respectively. A flavonoid glycoside (210 mgs) was isolated from ethyl acetate extracts by repeated column chromatography over silica gel of 60–120μ mesh size. There was highly significant recovery of rats form non-insulin dependent diabetes mellitus treated with KA (200 mg/kg p. o./day) for 2–3 weeks as per with following parameters: 1) Blood glucose level, ii) Effect on body weight, iii) Survival of the animals, iv) Water intake, urine output & presence of glucose in urine, v) General condition of the animals and vi) Visit of ants to the voided urine of the rats.

What we claim is:

1. A method of treating hyperglycemia and non-insulin dependent diabetes mellitus in an animal, comprising administering an effective amount of an *Argyrolobium roseum* extract to said animal for a period of time, wherein said extract comprises a flavonoid glycoside compound and optionally comprises a pharmaceutical additive.

2. The method of claim 1, wherein said method further comprises co-administering at least one pharmaceutically acceptable additive.

3. The method of claim 1, wherein said animal is a mammal.

4. The method of claim 3, wherein said animal is a human.

5. The method of claim 2, wherein said additive is selected from a group consisting of proteins, carbohydrates, sugar, talc, magnesium stearate, cellulose, calcium carbonate, and starch-gelatin paste.

6. The method of claim 2, wherein said additive is a pharmaceutically acceptable carrier, excipient, diluent, solvent or a hypoglycemic agent.

7. The method of claim 1, wherein said effective amount is from about 1 to about 3000 mg/kg p.o./day.

8. The method of claim 1, wherein said effective amount is from about 200 to about 1000 mg/kg p.o./day.

9. The method of claim 1, wherein said period of time is from about 2 to about 4 weeks.

10. The method of claim 1, wherein said extract produces no harmful side effect in said animal.

11. A purified composition comprising an effective amount of an *Argyrolobium roseum* extract, wherein said extract comprises a flavonoid glycoside compound.

12. The composition of claim 11, further comprising at least one additive.

13. The composition of claim 12, wherein said additive is selected from a group consisting of proteins, carbohydrates, sugar, talc, magnesium stearate, cellulose, calcium carbonate, and starch-gelatin paste.

14. The composition of claim 12, wherein said additive is a pharmaceutically acceptable carrier, excipient, diluent, solvent or a hypoglycemic agent.

15. The composition of claim 11, wherein said composition is formulated as a capsule, tablet, syrup, concentrate, powder, granules, aerosol, or bead.

16. A process for isolating a flavonoid glycoside compound-containing *Argyrolobium roseum* extract, comprising (a) drying a *Argyrolobium roseum* plant into power form; (b) percolating the powder about 3–5 times with polar or non-polar solvents to obtain an extract, (c) macerating the extract; (d) drying the extract in vacuum; and (e) isolating the flavonoid glycoside compound by chromatography, wherein said flavonoid glycoside compound has hypoglycemic activity.

17. The process of claim 16, wherein the flavonoid glycoside compound is isolated using a silica gel of 60–120 microns mesh size in a chromatography column.

18. The process of claim 16, wherein macerating the extract is performed in the presence of hexane, ethyl acetate, acetone, or chloroform.

19. The process of claim 16, wherein said percolating is performed using an alcohol or an acetone.

* * * * *